United States Patent [19]

Huffman

[11] Patent Number: 4,842,242
[45] Date of Patent: Jun. 27, 1989

[54] RIBBED FLEXIBLE MOLD FOR STRIATED DENTAL MODEL BASES

[75] Inventor: Ronald E. Huffman, Tucson, Ariz.

[73] Assignee: KV33 Corporation, Tucson, Ariz.

[21] Appl. No.: 9,276

[22] Filed: Jan. 30, 1987

[51] Int. Cl.[4] .................... A61C 13/01; B28B 7/06; B28B 7/20; B29C 33/42

[52] U.S. Cl. ........................... 249/54; 249/98; 249/127; 249/134; 249/183; 264/17; 264/313; 433/54; 433/60

[58] Field of Search .................... 264/16–19, 264/313; 433/222.1, 212.1, 223, 213, 214, 206, 207, 167, 60, 54; 425/2; 249/54, 175, 127, 183, 134, 98; 156/293, 303.1

[56] References Cited

U.S. PATENT DOCUMENTS

| | | | |
|---|---|---|---|
| 2,611,961 | 9/1952 | Neer | 433/60 |
| 2,629,929 | 3/1953 | Levine et al. | 433/60 |
| 3,409,489 | 11/1968 | Renton | 156/293 |
| 4,191,606 | 3/1980 | Evans | 156/293 |
| 4,214,367 | 7/1980 | Mack et al. | 433/60 |
| 4,265,619 | 5/1981 | Lucki et al. | 433/213 |
| 4,283,173 | 8/1981 | Browne et al. | 249/54 |
| 4,368,042 | 1/1983 | Felstead et al. | 433/213 |
| 4,481,162 | 11/1984 | Huffman | 249/54 |
| 4,496,320 | 1/1985 | Hwang et al. | 433/60 |
| 4,538,987 | 9/1985 | Weissman | 249/54 |

FOREIGN PATENT DOCUMENTS

| | | | |
|---|---|---|---|
| 2644797 | 4/1977 | Fed. Rep. of Germany | 433/213 |
| 2923208 | 12/1980 | Fed. Rep. of Germany | 433/60 |

Primary Examiner—Jan H. Silbaugh
Assistant Examiner—Karen D. Kutach
Attorney, Agent, or Firm—Victor Flores; Harry M. Weiss

[57] ABSTRACT

A flexible mold and method of forming a base defining either a full base or quadrant base of a dental model is provided with a perimeter member for defining the side walls of the base and a shelf extending inwardly from the rear side wall for delineating a slot at the rear of the base, which slot is usable for adhering an arm of an articulator. The configuration of the slot and/or the rear side wall of the base is striated for better adherence with the attached articulator.

8 Claims, 3 Drawing Sheets

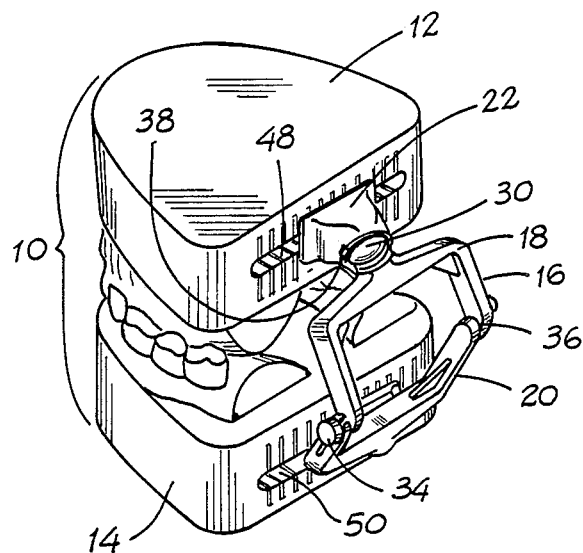
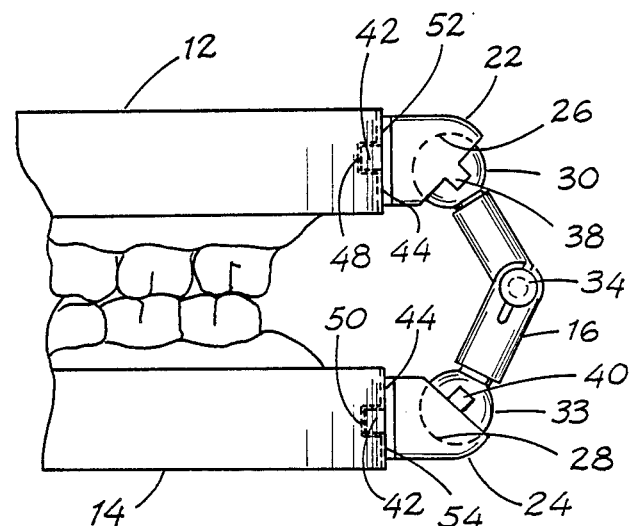
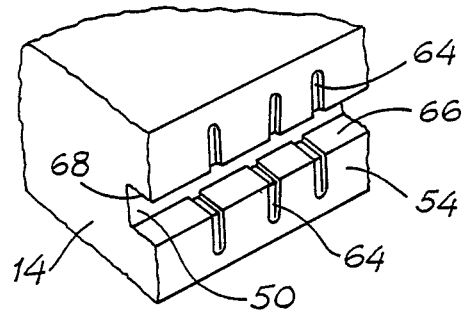
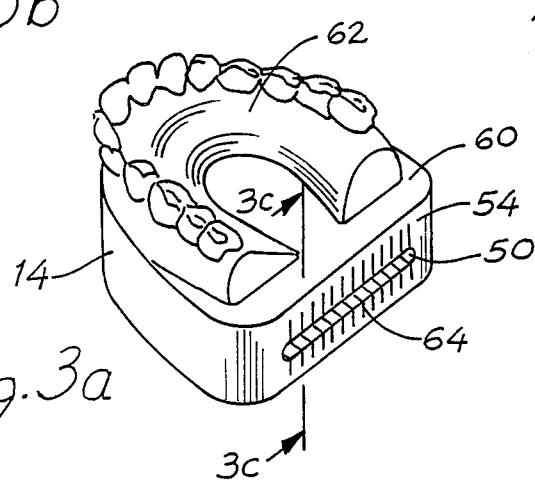
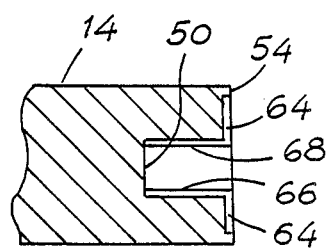
fig. 1
fig. 2
fig. 3b
fig. 3a
fig. 3c

RIBBED FLEXIBLE MOLD FOR STRIATED DENTAL MODEL BASES

RELATED U.S. PATENTS

The present application is directed to an improvement over the subject matter described in the following U.S. Pat. No. 4,481,162 entitled "Flexible Mold For Dental Model Bases and Method for Using It", No. 4,382,787 entitled "Dental Model Articulator" and No. 4,378,929 entitled "Mold for Dental Models"; No. 4,494,934 entitled "Dental Model Base"; No. Des. 283,541 entitled "Molded Full Base Dental Cast with Pedestal"; No. Des. 283,542 entitled "Molded Full Base Dental Cast"; Nos. Des. 283,639 entitled "Set of Molded Quadrant Base Dental Casts With Pedestal"; No. Des. 283,730 entitled "Molded Quadrant Base Dental Cast", all of these patents are assigned to the present assignee.

TECHNICAL FIELD

The present invention relates to dental models and, more particularly, to molds and methods for using same to form a base of a dental model and to bases formed from such molds.

BACKGROUND ART

To accurately form and position false teeth or caps, a dentist normally makes a negative impression of the affected tooth or teeth. The negative impression may be partial, unilateral or bilateral, depending upon the extent of work to be done; the negative impression serves as a mold for developing a die of the patient's tooth or teeth. The negative impression is obtained by partially filling a tray with thermoplastic material. The filled tray is inserted within the patient's mouth such that the teeth and adjacent gum sink into and create a cavity within the thermoplastic material. Shortly thereafter, the thermoplastic material will cure and retain an exact impression of the patient's teeth and adjacent gum. This is an essentially standard technique presently used by most dentists.

To form a tooth die, a pourable casting stone, known as pink stone is poured into the negative impression up to at least the margin or base of the tooth. The pink stone is compacted to preclude voids and remove any air bubbles. After the pink stone is at least partially cured, wax or similar lubricant is swathed upon the surface of the pink stone.

In the prior art, the base for the dental mold is made by one of two methods. First, additional pourable hardenable stone, generally referred to as yellow stone, is poured within the negative impression to cover the pink stone and the retainer with sufficient depth of yellow stone to form a solid base. After both the pink stone and the yellow stone have hardened, the tray and supported thermoplastic material is peeled away to leave a conventional dental model. Alternatively, a patty of yellow stone is formed upon a glass or other smooth surface. The partially or completely cured pink stone is placed thereupon.

In either method, pins are lodged or fixated in the pink stone to extend into and slidably engage the yellow stone. Usually, three pins per model tooth to be worked on are used. The pins serve the function of maintaining registration of the model tooth with respect to the remaining die.

Either of the prior art methods for making the base of yellow stone requires substantial technician time to manually form the yellow stone into an initial shape. After it is cured, further time is required for cutting and grinding away excess yellow stone material. The time spent and material wasted necessarily adds to the cost of the dental model to the ultimate detriment of the patient.

Either of the above processes for making the bases of dental models tends to result in each base being somewhat unique and individualized. When the dental models are placed upon a dental articulator to perform work on the dental model, a substantial amount of time and expertise is necessary to properly attach and align the upper and lower coacting dental models to reproduce the relationship of the patient's jaws. The requisite time for aligning the dental models is exacerbated by the nonuniformity of the dental model base configurations and thicknesses and requires yet further time and effort to positionally orient and attach each base upon its respective arm of the articulator.

The dental base described and illustrated in U.S. Pat. No. 4,378,929 is formed by pouring the yellow stone into a mold. The mold standardizes the width, breath, height and configuration of the base. Such standardization permits the use of indexing means in the bases to mount opposing bases of a dental model upon an articulator. Additionally, there is described and illustrated the use of an overhang for forcing a depression in the surface of the base to which the tooth die is attached, which depression delineates a platform. The tooth die (pink stone) is attached upon the platform. To sever a model tooth from the tooth die, mesial and distal saw cuts are made through the tooth die to a point just below the line of demarcation between the tooth die and the base. The line of demarcation is coincident with the surface of the platform. As the saw blade need not be angled to have the saw end clear the opposing quadrant of the tooth die, the depth of cut into the base may be minimized at a point just below the platform surface.

In U.S. Pat. No. 4,382,787, there is described an articulator attachable to opposed pairs of dental model bases through a mounting means. The articulator is particularly easily usable with size standardized bases for dental models of the type described in U.S. Pat. No. 4,378,929. One embodiment of the mounting means usable as part of the articulator includes a tab, tang or ridge for penetrable engagement with a slot formed in the rear sidewall of a dental model base.

DISCLOSURE OF THE INVENTION

The present invention is directed to a uniformly sized full or quadrant dental model base having a slot formed within the rear sidewall which slot and sidewall are enhanced for adherence with an articulator and to a method for making such a base. Optionally, the base may include a platform for supporting the tooth die, as described in U.S. Pat. No. 4,378,929.

It is therefore a primary object of the present invention to provide a standard sized base for a full or quadrant dental model and having a slot formed in the rear sidewall of the base, which slot is enhanced for adhesive engagement with an arm of an articulator.

Another object of the present invention is to provide a standard sized base having a slot in the rear sidewall, which sidewall is enhanced for adhesive engagement with an arm of an articulator.

Yet another object of the present invention is to provide a mold for making a base for a full or quadrant dental model, which mold includes a ribbed shelf for forming a striated slot in the rear sidewall of the base to enhance adhesive engagement between the base and arm of an articulator.

Still another object of the present invention is to provide a mold for making a base for a full or quadrant dental model, which mold includes a ribbed shelf for forming a striated slot in the rear sidewall of the base and ribs for forming striations in the rear sidewall of the base, which striated slot and striations enhance the adhesive engagement between the base and an arm of an articulator.

A further object of the present invention is to provide a flexible mold for making a base for a full or quadrant dental model, which mold includes ribs for forming striations in the rear sidewall of the base to enhance adhesive engagement between the base and an arm of an articulator.

A yet further object of the present invention is to provide a method for forming a slot in the rear sidewall of a base for a full or quadrant dental model which slot is enhanced for adhesive engagement with an arm of an articulator.

A still further object of the present invention is to provide a method for enhancing the rear sidewall of a base for a full or quadrant dental model for adhesive engagement with an arm of an articulator.

A still further object of the present invention is to provide a method for forming a slot in the rear sidewall of a base for a full or quadrant dental model and for enhancing the rear sidewall for adhesive engagement with an arm of an articulator.

These and other objects of the present invention will become apparent to those skilled in the art as the description thereof proceeds.

BRIEF DESCRIPTION OF THE DRAWINGS

The present invention may be described with greater specificity and clarity with reference to the following drawings, in which:

FIG. 1 is a perspective view of full dental model base constructed in accordance with the present invention and attached to an articulator;

FIG. 2 is a side view showing the bases of the present invention attached to an articulator;

FIG. 3a is a perspective view illustrating a dental model base constructed in accordance with the present invention; FIG. 3b illustrates a detail shown in FIG. 3a;

FIG. 3c is a cross sectional view taken along lines 3c—3c, shown in FIG. 3a;

FIG. 4b illustrates a detail shown in FIG. 4a;

FIG. 5 is a cross sectional view taken along lines 5—5, as shown in FIG. 4a;

BEST MODE FOR CARRYING OUT THE INVENTION

Figure 4A:
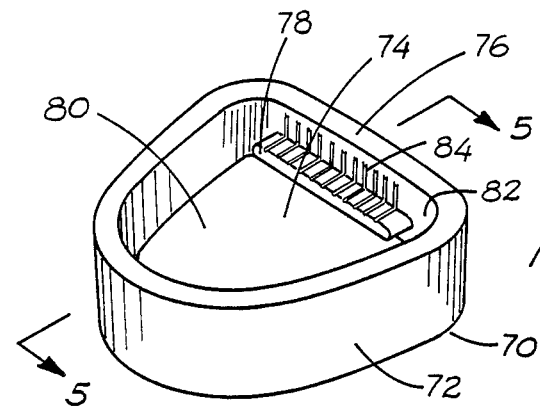
FIG. 4a illustrates a mold for making a model dental base.

In the practice of prosthetic dentistry, one very important technical problem is the shaping and fitting of the restoration occlusal surfaces to register, meet and operatively cooperate with opposed surfaces in conformity with the established habits, idiosyncrasies and tooth facet inclinations of the user. The many factors peculiar to the individual have heretofore made proper operative correlation of the restoration with the associated dental elements almost invariably a matter susceptible of satisfactory resolution only through repetitious adjustments and modifications had in the dental chair after installation of the restoration. This occurs despite the use of fixed, even though adjustable, mechanically simulated axis of articulation, planes and arcs of occlusion, lines, planes and axis of symmetry and the like which fail to provide the full orbital range necessary for reconstitution of the natural dental relationships determinable from the traces and indices upon and established through use of the original dentures. To facilitate attainment of the desired operative registration between restorations and their associated dental elements and thereby largely obviate the necessity for adjustments and corrections in the dental chair, the present invention provides dental model bases particularly configured to mate with a specifically configured articulator to prove a device for laboratory use by dentists or it can be fully and accurately portrayed and operatively duplicated as a check mounting for the restoration.

Referring to FIG. 1, there is shown a complete dental model 10 having a pair of mating full dental model casts 12 and 14 simulative of the original dentures and the condition requiring restoration or correction. An articulator 16 is attached to the casts to maintain them positionally simulative of the natural relationships portrayed when substantially in parallel relationship at one limit of the range of relative movement. A pair of interconnecting elements or brackets 18 and 20 are pivotally attached to one another and are of resilient flexible material sufficient to accommodate relative movement about all axis and within all planes between the casts in simulation of the operative range and pattern of the original dentures.

Referring jointly to FIGS. 1 and 2, further details of articulator 16 and its relationship to casts 12 and 14 will be described. First and second mounting means 22 and 24 are attached to casts 12 and 14, respectively. Each mounting means includes a semi-spherical or partially spherical depression disposed at the respective extremity; in example, mounting means 22 includes depression 26 and mounting means 24 includes depression 28. Brackets 18 and 20 include spheres 30, 33 sized to receivingly mate with depressions 26, 28, respectively. Brackets 18 and 20 are pivotally joined to one another by pivot means 34, 36; the pivot means may be flexible interconnection or of the snap fit type illustrated.

To mount articulator 16, mounting means 22 and 24 are attached to the rear sidewalls of the respective casts. Spheres 30 and 33 are located within the respective depressions 26, 28 upon angular adjustment of the respective brackets to obtain the requisite spatial relationship therebetween; nominally, the brackets define an interior obtuse angle. To maintain the casts in the predetermined fixed spatial relationship to one another at one limit of the range of relative movement, an adhesive is applied intermediate the spheres and their respective depressions to fixedly secure the respective brackets in fixed angular orientation with respect to the mounting means. Pivotal movement of the casts is effected by relative angular displacement between the joined brackets about the respective pivot means or hinge line. Translational movement in any plane and rotational movement about any axis of the casts with respect to one another is accommodated by the flexing of brackets 16 and 18.

Mounting means 22 and 24 may be generally triangular in one plane to provide an apex within which the depressions (26,28) are formed. To simplify manipulation of articulator 16 during attachment to the casts and fixation of the angular relationship between the brackets and the mounting means, retaining fingers 38 and 40 may be employed to extend from the perimeter of depressions 26, 28 respectively. These fingers are of resilient material and, in the quiescent state, cant toward one another to provide snap retention for a sphere inserted within the respective depressions. By the use of such fingers, the components of articulator 16 are retained attached to one another during positioning of casts 12 and 14. Upon achievement of the initial positioning orientation of the casts, an adhesive, such as any one of the commercially available fast setting cyanoacrylate, aerobic or anaerobic adhesives, may be employed to fixate each sphere within its respective depression.

Each of mounting means 22 and 24 incudes a tab, key or ridge 42, extending from planar side 44 of the respective mounting means. A receptacle, key way or slot 48, 50 is formed in rear sidewalls 52, 54, respectively, of bases 12, 14 to matingly receive the ridge of the respective mounting means. The resulting mechanical engagement between the mounting means and the casts, in combination with mastic or adhesive disposed therebetween, rigidly secures each mounting means to its respective cast.

Preferably, each slot 48, 50 is wider than the ridge to be inserted therein to permit lateral movement in attaching the respective mounting means thereto and to permit deliberate offset attachment of the articulator for particular purposes. Mounting means 22 and 24 are preferably of plastic and formed by any one of several available plastic forming techniques; thereby, the size, positioning and angular relationship between the ridge and the respective side mounting means can be controlled to close tolerances. Through the method to be described below, the height, width, length and configuration of each of bases 12 and 14 can be standardized and the configuration, positioning and angular orientation of slots 48, 50 with respect to the rear walls 52, 54 of the casts can be held to close tolerances. The resulting fit achievable between each slot and its ridge along with the parallelism achievable between the opposing adjacent sides and rear walls create a strong mechanical junction between each cast and the respective mounting means of the articulator. The further use of an adhesive to bond the mounting means to the casts insures maintenance of a fixed relationship therebetween.

Referring to FIG. 3a, there is shown a standard sized dental model cast 14 having a base 60 upon which has been mounted a model tooth die 62. A slot 50 extends horizontally inwardly from rear side wall 54; as described above, this slot receives a corresponding ridge 42 from one of the mounting means of the articulator. A method for securing the mounting means (24) to a cast (14) is by the application of an adhesive intermediate planar side 44 of the mounting means and rear sidewall 54 and between the surfaces of ridge 42 and the corresponding surfaces of slot 50. If the mounting means is held flush against the rear sidewall, penetrating of the adhesive intermediate the mounting means and the rear sidewall and slot must occur through wicking of the adhesive. Such wicking may be more or less effective in penetration throughout the juxtaposed surfaces of the mounting means and the rear sidewall and slot. To assure substantial wicking each and every time an adhesive is applied, channels 64 are formed in rear sidewall 54, which channels extend into the opposing sides of slot 50. As more particularly illustrated in FIGS. 3b and 3c, a plurality of channels 64 are dispersed along slot 50. These channels are depicted as being parallel with one another. Moreover, the channels formed in the lower part of the rear sidewall and extending into side 66 of channel 50 are in general alignment with the channels extending from the upper rear sidewall into side 68 of slot 50. It is to be understood that channels 64 are added for enhancing adhesive wicking action and do not require physical engagement with ridge 42. Further, channels 64 do not have to be parallel with one another or uniformly spaced along slot 50 nor do the channels have to be formed with opposing counterparts on either side of the slot.

With channels 64 developed in cast 14, any adhesive applied intermediate the mounting means and the rear sidewall of a cast will, by its own wicking action and by transport in channels 64, tend to flow essentially throughout the junction between planar side 44 of the mounting means and the corresponding rear sidewall and between the surfaces of ridge 42 and the corresponding areas of slot 50. The resulting spread of adhesive will help assure a more rigid and stable bond between the mounting means and the cast than is achievable without the presence of channels 64.

Referring jointly to FIGS. 4 to 8, a mold 70 for developing base 60 will be described. Mold 70 is formed as a monolithic unit of a rubber or rubber-like compound to provide sufficient rigidity to delineate the configuration of the base to be formed and yet permit outward bending and stretching of the mold sidewalls to effect release and removal of the formed base. An example of a suitable rubber compound is sold by the Friedheim Tool Supply Company under the mark JOFRE.

A continuous sidewall 72 extends upwardly from a substrate or floor 74. The junction therebetween may be sharp edged, as illustrated, or may be curved, depending upon manufacturing considerations attendant formation of the mold. Sidewall 72 includes a rear sidewall 76 for defining the planar rear wall 54 of base 60 to be formed (see FIG. 3a). A protrusion or shelf 78, which is preferably parallel with floor 74, extends inwardly into mold cavity 80. The shelf is disposed approximately midway up inner side 82 of rear sidewall 76. The shelf will form an indentation or slot in the base to be molded. A plurality of ribs 84, 86 are disposed upon the upper and lower surfaces of shelf 78, respectively. These ribs may extend from the edge of the shelf to inner side 82 of rear sidewall 76. Furthermore, ribs 84, 86 may extend upwardly and downwardly, respectively, on inner side 82 from the shelf, as illustrated. These ribs develop channels 64 in cast 60, as illustrated in FIGS. 3a, 3b and 3c.

Figure 5:
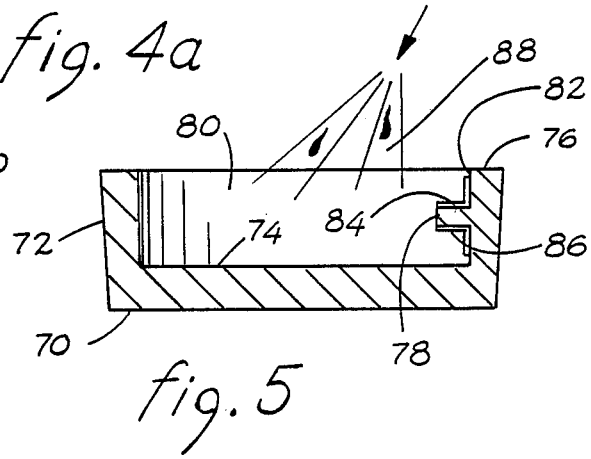
Figure 4B:
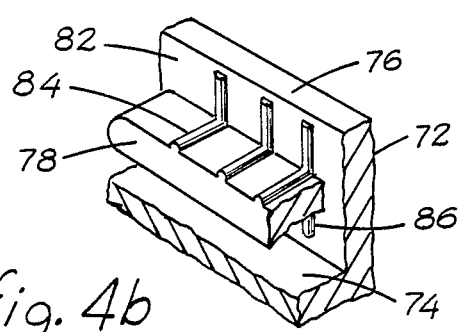
Figure 6:
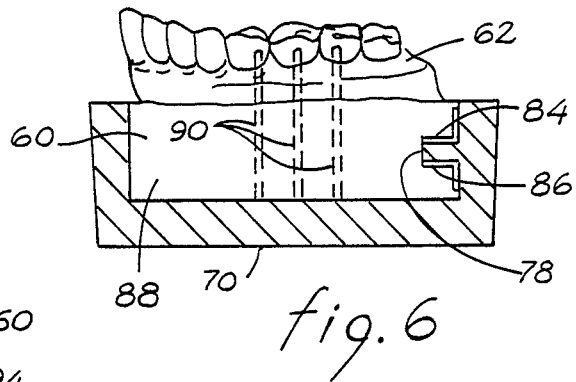
FIGS. 6, 7 and 8 illustrate a method for molding a standard sized dental model base.

To form a dental model cast 60 (see FIG. 3a), yellow stone 88 is a flowable state is poured into mold cavity 80, as illustrated in FIG. 5. The yellow stone will flow beneath and around shelf 78 and up to a level coincident with the top of continuous sidewall 72. A screed or the like may be employed to obtain a level top surface of the yellow stone. Before the yellow stone sets, a tooth die 62 (pink stone), having a plurality of dowels or pins 90 depending therefrom is placed upon the uncured exposed surface of base 60. Preferably, the extending part of pins 90 is commensurate in length with the thickness of base 60, as shown in FIG. 6; the pins are coated with a release agent to permit sliding engagement with the base after the yellow stone is cured.

Figure 7:
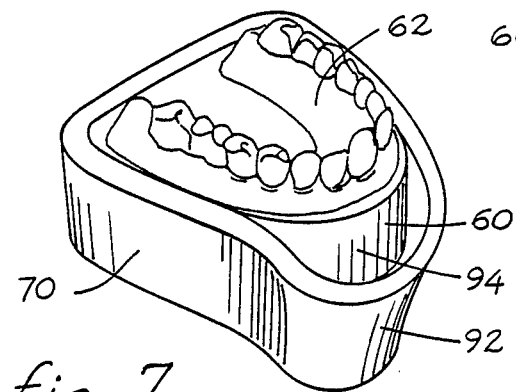

After curing of the yellow stone, front end 92 of continuous sidewall 72 is pried forwardly and downwardly away from the corresponding front 94 of base 60, as shown in FIG. 7, to permit manual grasping of the base. Thereafter, the base is pulled forwardly of mold 70 to permit sliding disengagement between shelf 78 and the resulting slot 50 formed in base 60 along with channels 64 formed in rear sidewall 54 and the slot; note in particular FIG. 8. Thereafter, the mold is released, which release permits it to resume its shape as depicted in FIG. 4a. The mold is now ready to be used in the making of a further full base 60. The dental model cast withdrawn from mold 70 corresponds to the configuration illustrated in FIG. 3a. It is now ready for attachment to articulator 16.

Figure 9:
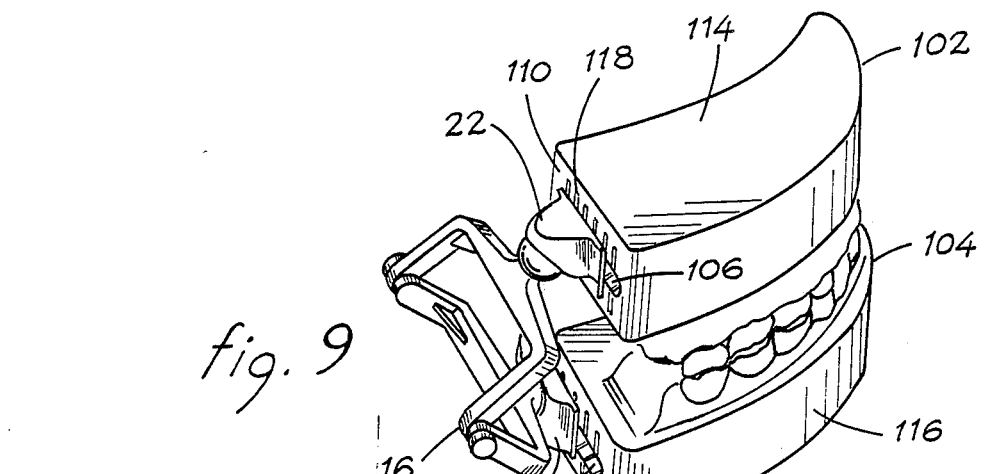
FIG. 9 is a perspective view of quadrant dental model bases constructed in accordance with the present invention and attached to an articulator.

Referring to FIG. 9, there is shown a complete dental model 100 having a pair of mating quadrant dental model casts 102, 104 simulative of the original dentures and the condition requiring restoration or correction. An articulator 16, like that shown and described with respect to FIGS. 1 and 2, is attached to the casts to maintain them positionally simulative of the natural relationships portrayed when substantially in parallel relationship at one limit of the range of relative movement. Mounting means 22, 24 each include a ridge 42 extending from planar side 44, of the respective mounting means. A slot 106, 108 is formed in rear wall 110, 112, respectively, of bases 114, 116 of casts 102, 104 to matingly receive the ridge of the respective mounting means.

As described above with respect to cast 14, a plurality of channels 118 are formed in the face or rear wall 110 in communication with slot 106. These channels may extend into one or both opposed sides of the slot. Alternatively, the channels may be formed only in one or both opposed sides of the slot.

Similarly, a plurality of channels 120 are disposed in rear wall 112 in communication with slot 108 or be limited to the slot. These channels may also extend into one or both of the opposed sides of slot 108. By employing such channels, wicking of the adhesive between planar side 44 of each of mounting means 22, 24 and the respective rear wall of casts 114, 118 is greatly encouraged. With the enhanced spread of adhesive, the bond formed on curing of the adhesive is likely to be quite robust. The resulting mechanical engagement between the mounting means and the casts, in combination with mastic or adhesive disposed therebetween, rigidly secures each mounting means to its respective cast.

Figure 10:
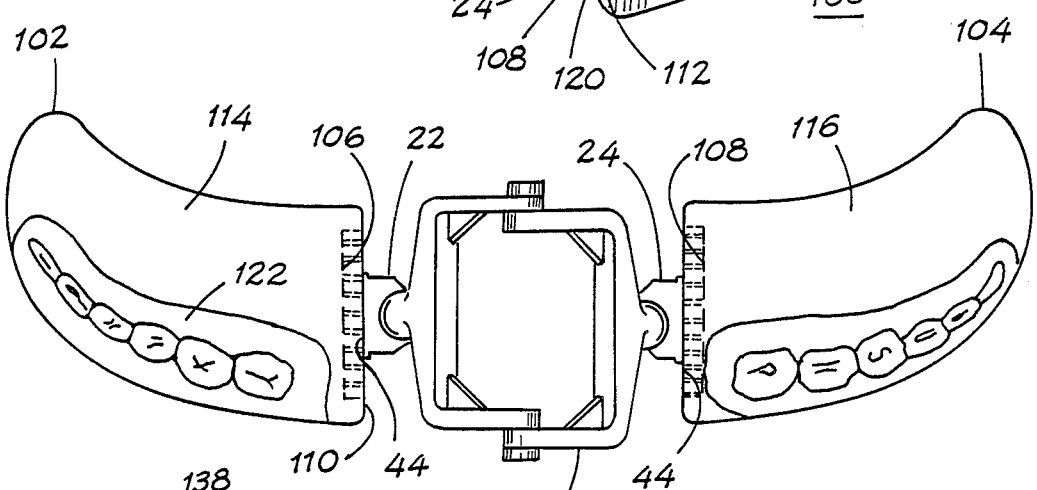
FIG. 10 is a top view illustrating opposing quadrant dental model bases attached to an articulator.

Referring to FIG. 10, there is shown a standard sized quadrant dental model cast 102 having a base 114 upon which has been mounted a model tooth die 122. Slot 106 extends horizontally inwardly from rear wall 110. As described above, this slot receives a corresponding ridge from one of the mounting means of the articulator.

A mold 130 for developing base 114 will be described with reference to FIG. 11. The mold is formed as a monolithic unit of rubber or rubber-like compound to provide sufficient rigidity to delineate the configuration of the base to be formed and yet permit outward bending and stretching of the mold sidewalls to effect release and removal of the formed base. A continuous sidewall 132 extends upwardly from substrate or floor 134. The sidewall includes a rear sidewall 136 for defining the planar rear wall 110 of the base (see FIG. 10). A shelf 138, which may be parallel with floor 134, extends inwardly into mold cavity 140. The shelf is disposed approximately midway up to the top of rear sidewall 136. To form channels 118 in cast 114, a plurality of ribs 142 are formed on the upper surface of shelf 138 and a further plurality of ribs 144 are formed in the lower surface of the shelf; see FIGS. 12 and 13. These ribs may extend rearwardly to the inside surface of rear wall 136 and extend therealong in opposed directions from shelf 138; alternatively, the ribs may be disposed only upon the surface of rear wall 136.

To form a quadrant dental cast 102 (see FIG. 10), yellow stone in a flowable state is poured into mold cavity 140. The yellow stone will flow beneath and around shelf 138 and up to a level coincident with the top of continuous sidewall 132. A screed or the like may be employed to obtain a level top surface of the yellow stone. Before the yellow stone sets, a tooth die 122 having a plurality of pins depending therefrom is placed upon the uncured exposed surface of the base. Preferably, the extending part of the pins is commensurate in length with the thickness of the base to be formed.

Figure 8:
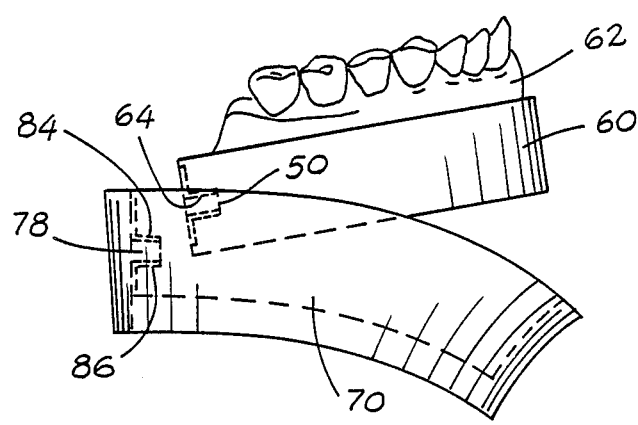

After the yellow stone has cured, front end 146 of continuous sidewall 132 is pried forwardly and downwardly away from the corresponding front of the base formed to permit grasping of the base. Thereafter, the base is pulled forwardly of mold 130 to permit sliding disengagement between shelf 138 and the resulting slot 106 formed in base 114. Reference may be made to FIGS. 7 and 8 for these steps.

Figure 11:
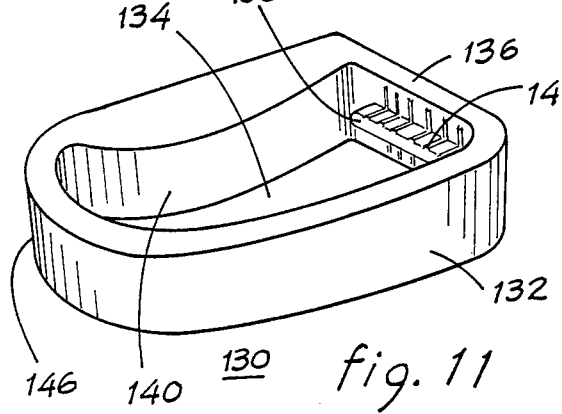
FIG. 11 illustrates a mold for making a quadrant dental model base.
Figure 12:
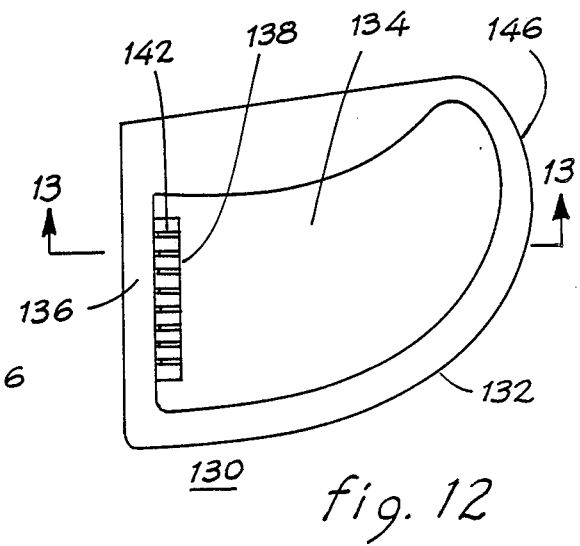
FIG. 12 is a top view of the mold shown in FIG. 11.
Figure 13:
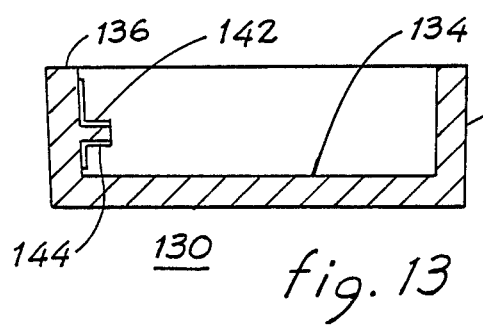
FIG. 13 is a cross sectional view taken along lines 13—13, as shown in FIG. 12.

In the above discussion attendant FIGS. 11 to 13, mold 130 for forming cast 114 has been discussed. It is to be understood that a mirror image of mold 130 is developed to obtain cast 116. All the elements and relationships described with respect to mold 130 would be incorporated in the mirror image of the mold. Thus, cast 116 is and would be a mirror image of cast 114.

While the principles of the invention have now been made clear in an illustrative embodiment, there will be immediately obvious to those skilled in the art many modifications of structure, arrangement, proportions, elements, materials and components, used in the practice of the invention which are particularly adapted for specific environments and operating requirements without departing from those principles.

I claim:
1. A flexible mold for forming a base of a dental model usable with an articulator, said base being formed from a pourable hardenable compound deposited therein, said mold comprising in combination:
(a) a flexible sidewall for defining a perimeter of a mold cavity having a planform that delineates the configuration of said base to be formed and having an upper edge for defining an opening to said mold cavity, said opening being dimensionally coincident with a maximum dimensional planform of said mold cavity;

(b) a flexible substrate for defining a flat bottom of said cavity, said substrate and said sidewall member cooperating to define said bottom and lateral surfaces of said mold cavity;

(c) a shelf attached to a limited portion of said sidewall and extending within said perimeter of said mold cavity along a projection axis parallel to said bottom and partially across said mold cavity, said shelf having a plurality of ribs disposed upon said shelf to define a ribbed shelf, said plurality of ribs extending upon said sidewall in proximity to said shelf, said ribbed shelf and said plurality of ribs extending upon said sidewall delineating a striated receptacle within said base and striations on said base in proximity to said receptacle for enhancing adhesive wicking action during attachment of said articulator to said base; and (d) said substrate and said sidewall being bendable in concert to lower a part of said upper edge of said sidewall across said mold cavity from said shelf to permit withdrawal of said base from said mold cavity along said projection axis of said shelf and allow sliding disengagement of said receptacle from said shelf.

2. A flexible mold for forming a base of a dental model usable with an articulator, said base being formed from a pourable hardenable compound deposited therein, said mold comprising in combination:

(a) a flexible sidewall for defining a perimeter of a mold cavity having a planform that delineates the configuration of said base to be formed and having an upper edge for defining an opening to said mold cavity, said opening being dimensionally coincident with a maximum dimensional planform of said mold cavity;

(b) a flexible substrate for defining a flat bottom of said mold cavity, said substrate and said sidewall member cooperating to define said bottom and lateral surfaces of said mold cavity;

(c) a shelf attached to a limited portion of said sidewall and extending within said perimeter of said mold cavity along a projection axis parallel to said bottom and partially across said mold cavity, said shelf delineating a receptacle within said base to which said articulator may be attached;

(d) ribs disposed along said sidewall and extending within the perimeter of the mold cavity for delineating a striated surface on said base to which said articulator may be better adhesively attached due to increased wicking action produced by said striated surface, said ribs being disposed upon said sidewall in proximity to said shelf for forming a plurality of striations on said base in proximity to said receptacle; and (e) said substrate and said sidewall being bendable in concert to lower a part of said upper edge of said sidewall across said mold cavity from said shelf to permit withdrawal of said base from said mold cavity along said projection axis of said shelf and allow sliding disengagement of said receptacle from said shelf.

3. The mold as set forth in claim 2 wherein said ribs are parallel with one another.

4. A flexible mold for forming a base of a dental model usable with an articulator, said base being formed from a pourable hardenable compound deposited therein, said mold comprising in combination:

(a) a flexible sidewall for defining a perimeter of a mold cavity having a planform that delineates the configuration of said base to be formed and having an upper edge for defining an opening to said mold cavity, said opening being dimensionally coincident with a maximum dimensional planform of said mold cavity;

(b) a flexible substrate for defining a flat bottom of said cavity, said substrate and said sidewall member cooperating to define said bottom and lateral surfaces of said mold cavity;

(c) a ribbed shelf attached to a limited portion of said sidewall and extending within said perimeter of said mold cavity along a projection axis parallel to said bottom and partially across said mold cavity, said ribbed shelf delineating a striated receptacle within said base for enhancing adhesive wicking action during attachment of said articulator to said base;

(d) a plurality of ribs further disposed upon said sidewall in proximity to said shelf for forming a plurality of striations on said base in proximity to said receptacle, said plurality of striations being provided for enhancing adhesive attachment of said articulator due to increased wicking action produced by said plurality of striations; and (e) said substrate and said sidewall being bendable in concert to lower a part of said upper edge of said sidewall across said mold cavity from said shelf to permit withdrawal of said base from said mold cavity along said projection axis of said shelf and allow sliding disengagement of said receptacle from said shelf.

5. The mold as set forth in claim 4 wherein said plurality of ribs comprises ribs that are parallel with one another.

6. A flexible mold for forming a base of a dental model usable with an articulator, said base being formed from a pourable hardenable compound deposited therein, said mold comprising in combination:

(a) a flexible sidewall for defining a perimeter of a mold cavity having a planform that delineates the configuration of said base to be formed and having an upper edge for defining an opening to said mold cavity, said opening being dimensionally coincident with a maximum dimensional planform of said mold cavity;

(b) a flexible substrate for defining a flat bottom of said cavity, said substrate and said sidewall member cooperating to define said bottom and lateral surfaces of said mold cavity;

(c) a shelf attached to a limited portion of said sidewall and extending within said perimeter of said mold cavity along a projection axis parallel to said bottom and partially across said mold cavity, said shelf having a plurality of ribs disposed upon said shelf to define a ribbed shelf, said plurality of ribs being oriented parallel with said projection axis, said ribbed shelf delineating a striated receptacle within said base for enhancing adhesive wicking action during attachment of said articulator to said base; and (d) said substrate and said sidewall being bendable in concert to lower a part of said upper edge of said sidewall across said mold cavity from said shelf to permit withdrawal of said base from said mold cavity along said projection axis of said shelf and allow sliding disengagement of said receptacle from said shelf.

7. The mold as set forth in claim 6 wherein said plurality of ribs extend upon said sidewall in proximity to said shelf for forming a plurality of striations on said base in proximity to said receptacle.

8. The mold as set forth in claim 7 wherein said plurality of ribs extending upon said sidewall are parallel with one another.

* * * * *